United States Patent
Kristoffersen et al.

(10) Patent No.: US 8,792,295 B2
(45) Date of Patent: Jul. 29, 2014

(54) METHOD AND SYSTEM FOR MONITORING A TRANSDUCER ARRAY IN AN ULTRASOUND SYSTEM

(75) Inventors: Kjell Kristoffersen, Oslo (NO); Geir Haugen, Oslo (NO); Morten Lennart Haugen, Tonsberg (NO); Anders R. Sornes, Oslo (NO)

(73) Assignee: General Electric Company, Schenectady, NY (US)

( * ) Notice: Subject to any disclaimer, the term of this patent is extended or adjusted under 35 U.S.C. 154(b) by 374 days.

(21) Appl. No.: 13/362,890

(22) Filed: Jan. 31, 2012

(65) Prior Publication Data
US 2013/0194891 A1 Aug. 1, 2013

(51) Int. Cl.
*H04B 17/00* (2006.01)

(52) U.S. Cl.
USPC .......................................... 367/13

(58) Field of Classification Search
CPC .................................................. A61B 8/14
USPC ................................. 367/13, 11, 7
See application file for complete search history.

(56) References Cited

U.S. PATENT DOCUMENTS

| 4,475,376 A | 10/1984 | Keilman |
| 5,517,994 A | 5/1996 | Burke et al. |
| 5,676,149 A | 10/1997 | Yao |
| 7,155,957 B2 | 1/2007 | Gessert et al. |
| 7,278,289 B2 | 10/2007 | Gessert et al. |
| 8,002,704 B2 | 8/2011 | Torp et al. |
| 2009/0260443 A1 | 10/2009 | Suita et al. |
| 2010/0122566 A1 | 5/2010 | Kim |
| 2013/0194891 A1* | 8/2013 | Kristoffersen et al. ......... 367/13 |

FOREIGN PATENT DOCUMENTS

JP 2013154169 A * 8/2013

* cited by examiner

*Primary Examiner* — Daniel Pihulic
(74) *Attorney, Agent, or Firm* — The Small Patent Law Group; Dean D. Small (57) ABSTRACT

Methods and systems for monitoring a transducer array in an ultrasound probe are provided. One method includes acquiring ultrasound data using an ultrasound probe during an imaging mode of operation, wherein the ultrasound data includes echo information. The method further includes comparing the echo information from a plurality of transducer elements of a transducer array of the ultrasound probe during the imaging mode of operation, wherein the echo information is non-beamformed signal data. The method also includes determining non-uniformity information for the transducer array using the compared echo information during the imaging mode of operation.

22 Claims, 8 Drawing Sheets

Number Of Failed Elements :_

Compensated Elements :_

Predicted Remaining Probe Life :_

METHOD AND SYSTEM FOR MONITORING A TRANSDUCER ARRAY IN AN ULTRASOUND SYSTEM

BACKGROUND OF THE INVENTION

Diagnostic medical imaging systems typically include a scan portion and a control portion having a display. For example, ultrasound imaging systems usually include ultrasound scanning devices, such as ultrasound probes having transducers that are connected to an ultrasound system to control the acquisition of ultrasound data by performing various ultrasound scans (e.g., imaging a volume or body). The ultrasound systems are controllable to operate in different modes of operation to perform the different scans. The signals received at the probe are then communicated and processed at a back end.

The transducers in medical ultrasound probes typically contain array(s) having a large number of transducer elements, which may include associated per-element electronic circuits. The probes may be mechanically fragile, so it is common to experience degradation or even defects of some elements during the lifetime of the probe. One cause of failures is mechanical shock, for example if the probe is dropped on the floor. Other causes of failures may be the failure of electrical interconnects, partial delamination of the transducer lens or other acoustic layers, local depolarization of piezoelectric material, etc. Element degradation will deteriorate the quality of the image produced by the probe. In conventional systems, it is difficult or impossible to diagnose the array uniformity (or "health state") of a probe without use of special test equipment and/or test modes of the system. These know systems include the use of special test circuitry, use of special test objects, or use of special test modes. In some systems, special test software may be provided on the console, for example that includes "imaging" using only a single element of the probe, and having the operator step through the array under test one element at a time. This test is cumbersome, and, while it can be used to show the presence of elements that are defective, it is hard to obtain quantitative information from the test. Typically such a test would be performed by a service technician, and not by a sonographer. Thus, these known methods for diagnosis, if even possible to perform, are very time consuming and can be costly.

BRIEF DESCRIPTION OF THE INVENTION

In accordance with one embodiment, a method for monitoring a transducer array of an ultrasound probe when it is performing its normal imaging operation is provided. The method includes acquiring ultrasound data using an ultrasound probe during an imaging mode of operation, wherein the ultrasound data includes echo information. The method further includes comparing the echo information from a plurality of transducer elements of a transducer array of the ultrasound probe during the imaging mode of operation, wherein the echo information is non-beamformed signal data. The method also includes determining non-uniformity information for the transducer array using the compared echo information during the imaging mode of operation.

In accordance with another embodiment, an ultrasound system is provided that includes an ultrasound probe having a transducer array for acquiring ultrasound data including echo information during an imaging mode of operation and a memory for storing received echo information. The ultrasound system further includes a monitoring module for comparing the echo information from a plurality of transducer elements of the transducer array of the ultrasound probe during the imaging mode of operation, wherein the stored echo information is non-beamformed signal data. The monitoring module also determines non-uniformity information for the transducer array using the compared echo information during the imaging mode of operation.

In accordance with yet another embodiment, a non-transitory computer readable storage medium for monitoring a transducer array of an ultrasound probe using a processor during an imaging mode of operation is provided. The non-transitory computer readable storage medium includes instructions to command the processor to compare echo information from a plurality of transducer elements of a transducer array of an ultrasound probe during the imaging mode of operation, wherein the echo information is non-beamformed signal data. The non-transitory computer readable storage medium includes instructions to further command the processor to determine non-uniformity information for the transducer array using the compared echo information during the imaging mode of operation.

DETAILED DESCRIPTION OF THE INVENTION

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for monitoring the response of the individual transducer elements (or groups of elements) of an ultrasound probe using the ultrasound console, during normal scanning on the human body. By practicing various embodiments, and a technical effect of at least one embodiment, is that monitoring and/or diagnosis of an ultrasound transducer array without use of special test circuitry/test modes or test phantoms may be provided.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

Figure 1:
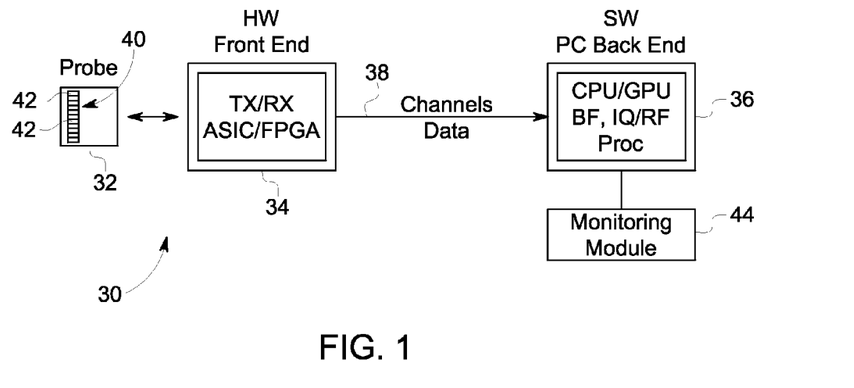
FIG. 1 is a simplified block diagram of an ultrasound system formed in accordance with various embodiments.

In various embodiments, ultrasound processing to form images is performed, for example, including ultrasound beamforming, such as receive beamforming, in software, hardware, or a combination thereof. One implementation of an ultrasound system having a software beamformer architecture formed in accordance with various embodiments is shown in FIG. 1, which illustrates a simplified block diagram of an ultrasound system 30. The ultrasound system 30 is configured to acquire ultrasound data using a probe 32 having a transducer array 40 (with a plurality of transducer elements 42), wherein transmission and reception functionality, such as transmission and reception of ultrasound signals are provided by a front end 34. In another embodiment, the probe 32 may contain electronics, for example, for performing partial beamforming of groups adjacent elements (such as using a SAP—Sub Array Processor) and/or transmitter electronics. In the illustrated embodiment, the front end 34 does not include a hardware implemented receive beamformer. However, it should be noted that a hardware implemented receive beamformer optionally may be provided to perform, for example, partial beamforming of groups of channels data 38. The front end 34 generally includes a transmitter/receiver, which may be implemented in, for example, an application specific integrated circuit (ASIC) or a field-programmable gate array (FPGA).

The transducer elements 42 may have a one-dimensional, two-dimensional, or three dimensional arrangement. Additionally, different types of transducer arrays 40 may be provided, such as a linear array or an arcuate array.

The front end 34 is connected to a back end 36, for example, via one or more communication lines (or channels data) 38, which may include one or more buses, such as a Peripheral Component Interconnect Express (PCIe) bus or other bus (e.g., a high bandwidth bus typically having several GB/sec. transfer rate). Alternately the communication channel may be a wireless link. The communication line(s) 38 communicates ultrasound data from the front end 34 to the back end 36, and may include one or more data channels. The data that is communicated from the front end 34 to the back end 36 is generally a digitized and optionally transformed version of the channel data as acquired by the probe 32. The transformation may include, for example, filtering/decimation, complex demodulation, or other standard signal processing operations.

The back end 36 generally includes processing units, which include a software implemented beamformer and an IQ/RF processor as described in more detail below. The processing functions may be performed by a general purpose CPU or GPU.

In various embodiments, the data transmitted from the front end 34 to the back end 36 is used to monitor the transducer elements 42 in real-time, for example, as the probe 32 is operating, such as scanning an object of interest. As described in more detail herein, the data is used to monitor an array response or uniformity of the transducer array 40 in real-time (e.g., during normal scanning operations). In particular, the various embodiments may use signals for all or a subset of the transducer elements 42 to perform real-time analysis of the transducer array 40.

In some embodiments, the ultrasound system 30 operates to perform real-time three-dimensional (3D) or four-dimensional (4D) scanning that transmits and/or acquires multiple beams simultaneously or concurrently. The ultrasound system 30 in various embodiments includes the software beamformer implemented in a general purpose processor (e.g., CPU or GPU) that receives data from a plurality of channels 38 corresponding to the transducer elements 42. Thus, data transfer from all or a subset of the channels 38 is provided in some embodiments for use in monitoring or analysis of the transducer array 40, which may be performed by a monitoring module 44 in the back end 36. The transferred data may then be beamformed with the general purpose processor performing, for example, beamforming calculations using any suitable beamforming method.

It should be noted that software beamforming includes performing any type of beamforming technique, which may include performing beamforming techniques in software that can be performed in hardware. It also should be noted that when reference is made herein to beamforming techniques, this generally refers to any type of image forming that may be performed by the ultrasound system. Accordingly, the various embodiments may be implemented in connection with forming images whether or not beams are formed.

Figure 2:
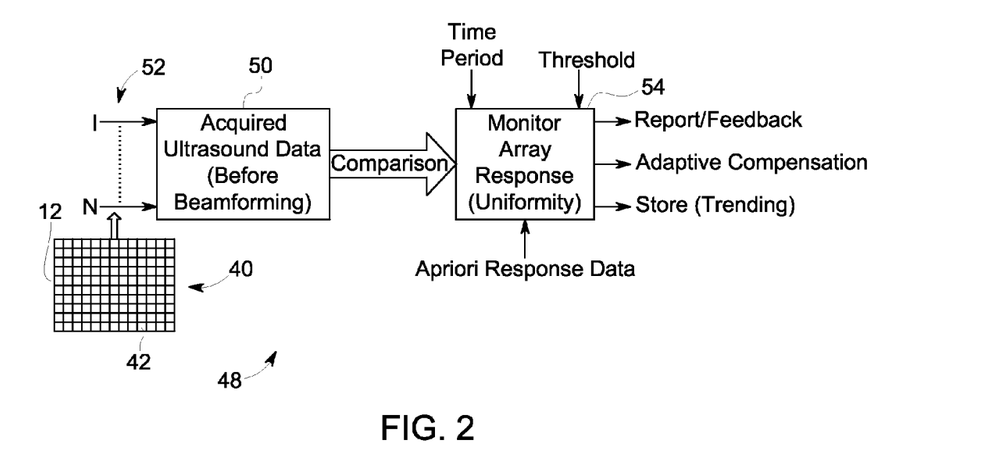
FIG. 2 is a block diagram illustrating an ultrasound processing work flow performed in accordance with various embodiments.

FIG. 2 illustrates an ultrasound processing work flow 48 performed in accordance with various embodiments for monitoring or analyzing the operation of the transducer elements 42 of the transducer array 40. In particular, acquired ultrasound data 50 is received via a plurality of receive channels 52. The acquired ultrasound data 50 is non-beamformed (or optionally sub-array beamformed) data in various embodiments, which may be stored temporarily, such as for a time frame on the order of that needed to align the phase fronts of the different signal channels (e.g., 1-15 micro-seconds) for use in performing monitoring and analysis operations. Thereafter, the acquired ultrasound data 50 is beamformed using a software beamformer.

The temporarily stored acquired ultrasound data 50 is used to monitor an array response to determine an array uniformity in real-time. For example, in one embodiment, the response of the individual transducer elements 42 (or groups/sets of the transducer elements 42, or output from electronics associated with one or more elements of the transducer array 40) are monitored during normal scanning operation of the probe 32, such as when scanning a patient. The monitoring of the response generally includes analyzing the echo signals from all or a subset of the transducer elements 42. In various embodiments, the analysis includes a comparison of the amplitudes from adjacent transducer elements 42. Using the comparison, and as described in more detail herein, an array response 54 is monitored, such as to determine an array uniformity.

The monitoring of the transducer array 40 using the echo responses may include using apriori response data to predict image quality deterioration as described in more detail herein. Additionally, the time period for analysis (e.g., averaging response data) may be varied and thresholding may be used to determine when a valid output signal suitable for analysis is detected. The results of the monitored transducer array 40 may be used to provide different outputs or may be used as an input to other processes. For example, the monitoring results may be used to generate a report or provide feedback useful in evaluating the condition of the probe 32 and whether, for example, any failure of transducer elements 42 may be as a result of misuse (e.g., an excessive acceleration event such as dropping or hitting of the probe 32). Additionally, the monitoring results may be used to provide adaptive compensation to improve or even fully correct imaging performance in the case of significant array non-uniformity. The monitoring results also may be stored for future use, such as for trending. In general, the results of the analysis, for example, the comparison of the response of the transducer elements 42 may be used in any way for evaluation of probe operation or to compensate for non-uniformities in the detector array 40. In some cases, such as in piezoelectric accidental de-poling, the various embodiments may incorporate some probe repair capability. For example, correction software may be provided that incorporates control of all (or a subset of) potential risk associated with probe characteristics changes relative to relevant safety regulations.

Figure 3:
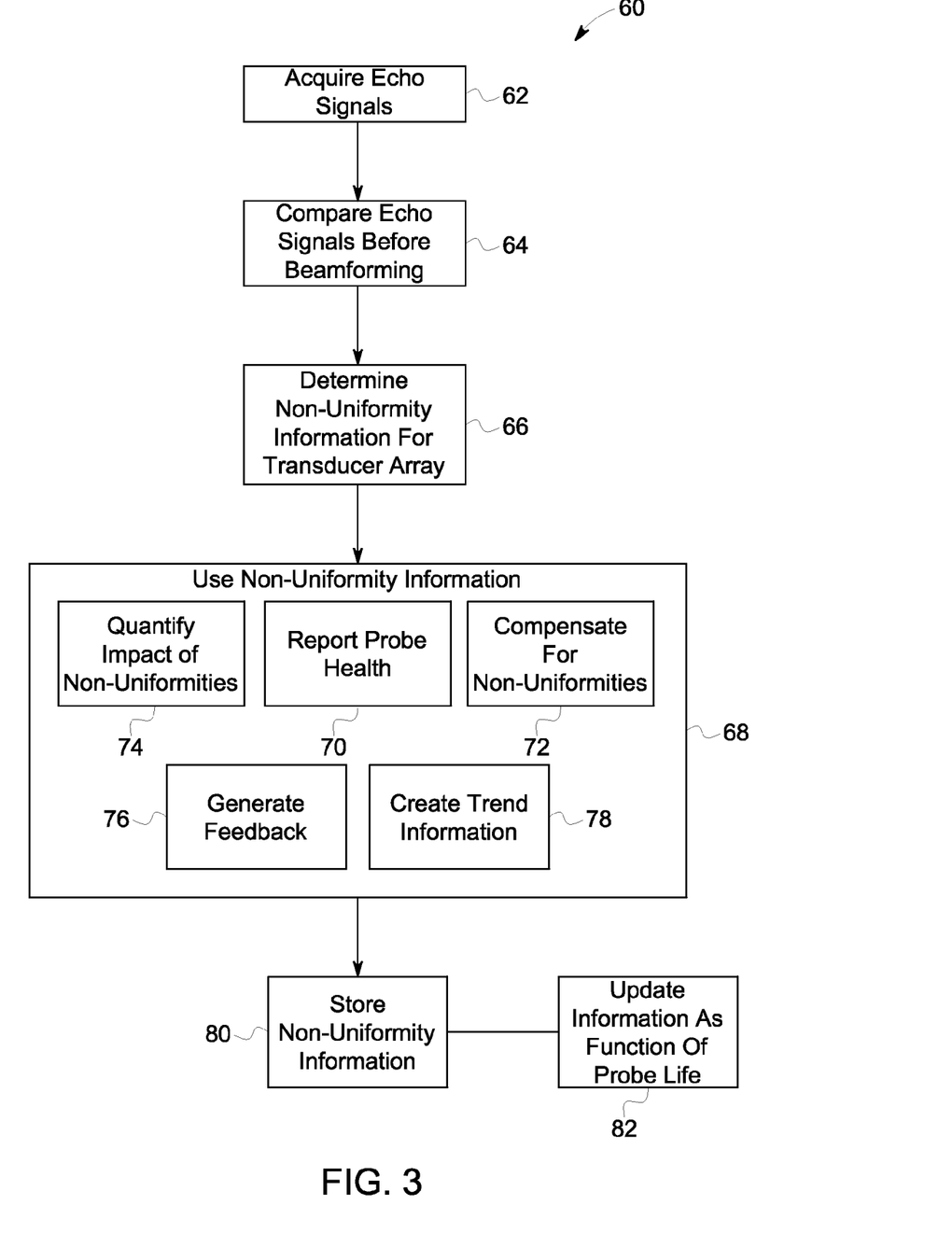
FIG. 3 is a flowchart of a method for monitoring a transducer array in accordance with various embodiments.

Various embodiments provide a method 60 as shown in FIG. 3 for monitoring a transducer array, for example, the transducer array 40, which includes analyzing the operation of the transducer elements of the transducer array. The method 60 including the monitoring of the transducer array is performed during an imaging mode of operation of the probe, for example, when the probe is performing a normal imaging operation. Thus, the method 60 in various embodiments allows for monitoring the probe while the probe is performing a particular operation, for example, when connected to an ultrasound console to scan tissue (e.g., human tissue) and produce images. Accordingly, in various embodiments, no test mode or special test object is needed or used.

The method 60 includes acquiring ultrasound data at 62, which includes acquiring echo signals from the ultrasound probe (e.g., the probe 32). In various embodiments, the acquired echo signals are signals as acquired by the probe, such that the ultrasound data is in a non-beamformed and/or non-image formed state. In one embodiment, for example, the ultrasound data is the signals received directly from the transducer elements of the transducer array, or some transformed version of those signals. Thus, the probe acquiring the ultrasound data does not beamform the data (except some embodiments that may use Sub-Array Beamforming in the probe; in such cases the ultrasound data corresponds to the output from the Sub-Array Processors within the probe). Instead, the ultrasound data is temporarily stored for use in the method 60 before being beamformed or otherwise processed by a software beamformer.

The method 60, in one embodiment, preprocesses the received raw signals before analyzing the signals as described below. For example, the raw signals are preprocessed to determine when the transducer is providing a valid output suitable for detection. In one embodiment, automatic thresholding of signal levels, or manually through an operator input is used to identify signals that exceed, for example, a minimum signal amplitude, such that the signal is a valid echo signal and not, for example, noise or crosstalk. In one embodiment with a manual identification, the operator may push a button when a "good" signal is present. Alternately, the ultrasound console may determine that a good signal is present when the operator performs certain operations (e.g., hitting the "store image" button). Alternately, the methods described in U.S. Pat. No. 8,002,704 may be used as an indication for good probe contact with the body, and, therefore, valid echo data. Still another example is to use the echoes from a transducer/lens ringdown, such as described in U.S. Pat. No. 5,517,994. These echoes are always present, but may be challenging to monitor reliably because the echoes occur so close to the large transmit pulse. In some advanced front-end configuration transducers, impedance may also be monitored.

Thereafter, the acquired echo signals are analyzed, for example, the echo signals are processed to monitor an array uniformity in real-time while the probe is scanning. For example, in one embodiment, the echo signals, which are the raw signals, are compared. Thus, the acquired signals before beamforming are compared. In particular, the echo signals from a plurality or all of the probe elements are compared in real-time, during normal scanning, without the use of special test objects, to measure and monitor array uniformity. In one embodiment, echo signals from adjacent probe elements are compared.

Thus, in various embodiments using ultrasound systems with software beamformers, the main echo processing unit has real-time access to the individual signals from the transducer elements, and the method 60 monitors the signals from the individual elements during normal scanning (e.g., compares signals from different transducer elements). A probe in perfect working condition is expected to have transducer elements that yield signals of similar amplitudes and predictable delay/phase characteristics during normal scanning. Accordingly, signals from any given element may be compared with the signals from neighboring or adjacent elements during normal scanning to determine variances.

For example, amplitudes of the signals from adjacent probe elements are compared, such as to determine if any exceed a predetermined difference variance. Alternately, for probes containing Sub-Array Beamformers (also referred to as "smart probes"), signals from a group of probe elements corresponding to the outputs of the Sub-Array Beamformers (SAPs) are compared. It should be noted that although the method 60 is described in connection with probes without SAPs, the method 60 may similarly be used with probes having SAPs.

The comparison in some embodiments may be performed using a simple comparison of the average echo amplitude for selected regions of interest. Alternately, in some embodiments correlation techniques between signals from adjacent elements may be used. In this case, and as described in more detail below, the element signals may be corrected for the expected time-of-flight difference for signals from a certain point in space (also referred to as beamforming delays) prior to performing the correlation. As another variation, the entire or part of this correction may be performed on the correlated result. The correlation analysis may be used to extract systematic time-of-flight errors for the probe, etc.

The measurements performed by the method 60 including the comparison of the echo signals may be performed in different ways. For example, the comparison at 64 may be performed with a relatively short averaging time, or the raw measurement results may be averaged over multiple measurement sessions, which can improve reliability. The average magnitude, the accumulated sum of signal magnitude or other statistical measures of the individual channel signals can be calculated over a very large time window compared to daily use of the machine such as to effectively average out the effects of different scanning views, different subjects or different machine setups, such that channel deficiencies can be more easily identified. It should be noted that the overall gain level summed over all channels also may be accumulated over a very large time scale and the accumulated value or the sliding average over this "historical" time scale may be monitored to identify a general weakening of the overall probe signal. The statistical window used in various embodiments has a time period such that scanning different subjects or scanning in air can be assumed to be averaged out. It also should be noted that in various embodiments, some function of the data, namely the channel data may be averaged, such as a relative channel sensitivity or other function related to the array sensitivity.

Thus, using the comparison at 64, non-uniformity information for the transducer array is determined at 66. For example, changes in array uniformity may be tracked over time, thereby allowing the ultrasound console to adaptively change the way the probe is controlled as described in more detail below. Accordingly, the deterioration of image quality introduced by the change in array characteristics may be reduced or minimized.

The non-uniformity information is then used at 68 to provide one or more outputs or perform additional operations. Thus, an ultrasound system of various embodiments that is capable of measuring and comparing probe element data may use the data in different ways, which will now be described in connection with various exemplary additional steps for the method 60.

For example, probe health may be reported at 70. For example, changes in probe health may be reported as a status to the operator. In one embodiment, a warning (e.g., an audible or visual notification), or quantitative information (e.g., numbers or graphs) may be generated and presented to an operator, for example, on a display of the ultrasound system.

The method 60 may also include compensating for the determined non-uniformities at 72. For example, alternately or additionally, adaptive compensation for element non-uniformities through changes in scanner setup may be provided. In one embodiment, a delay error may be compensated through changes in transmit or receive delays (tx and/or rx delays) in the beamforming. For example, a weak element may have a gain increase applied thereto on receive, and/or use a stronger excitation signal on transmit. Alternately the gain of immediate neighbor transducer elements may be increased if the transducer element is not functioning, not properly functioning, or "dead", such as, for example as described in U.S. Pat. No. 5,676,149.

The method additionally may include quantifying an impact of the non-uniformities at 74. For example, knowledge of the response of the individual array elements optionally allows for the prediction of image quality deterioration associated with that performance. In one embodiment, suitable simulation software and/or decision criteria may be used such that an "intelligent decision" may be made to determine if the current probe health is such that the probe should be replaced. It should be noted that knowledge of the individual element responses may also enable the console to adaptively compensate for changes in array non-uniformities (as described above in connection with step 72), thereby reducing or minimizing the image quality deterioration originating from a given probe health state.

For example, alternately or additionally, the data (with or without the compensations from steps 72 and 74) may be used as an input to a software simulator that quantifies the impact of the given probe health status on the transmit and/or receive beam response of the transducer. The simulator results may be used to identify failures that represent image quality deterioration and that also have a greater likelihood of interfering with the overall diagnostic use of the probe.

It should be noted that the health state of the probe at the time of a particular patient examination, or some performance index relating to the probe/system combination, where compensation mechanisms have been taken into account, may optionally be stored as a field in a patient examination report. This may serve, for example, as proof that the investigation was performed with a system in good working condition.

The measurement data also may be combined with other information to provide feedback at 76. For example, the probe may contain an acceleration or shock sensor, for example as described in U.S. Patent Application Publication 2006/0004290, which may be any suitable and/or commercially available device. In this embodiment, if the ultrasound console detects that:

a. the probe has been dropped (from the state of the shock sensor, optionally in combination with temporal information as to when the shock occurred), and b. this drop coincides with a deterioration of array uniformity, then this information may be provided as feedback (e.g., visual notification) to the operator, which may reduce the likelihood for similar events in the future. If such an event occurs within the warranty period of the probe, probe abuse may be concluded and the warranty of the probe may be voided.

Additionally, the method 60 may include creating trend information at 78. For example, the determined non-uniformity information may also be stored for future use, either in the ultrasound console and/or on a memory device in the probe assembly. Accordingly, trend information may be created that tracks the performance of the probe over time even if the probe is moved between different consoles.

Also, consoles that implement the method 60 may adaptively use compensation techniques to reduce or minimize the image quality impact of array non-uniformities that develop over the time of probe usage.

The non-uniformity information may be stored at 80, such as for subsequent use as described above or for later retrieval. In one embodiment, the information is stored such that the information is uniquely linked to the probe that is being monitored, tested or investigated, for example, by including or combining probe type with probe serial number information or some other unique identification label. For example, the stored non-uniformity information (e.g., probe health information) may be accessed (e.g., remotely accessed) by service technicians over a network. Additionally, updated information as a function of probe life may be stored at 82, such as updated non-uniformity information.

Figure 4:
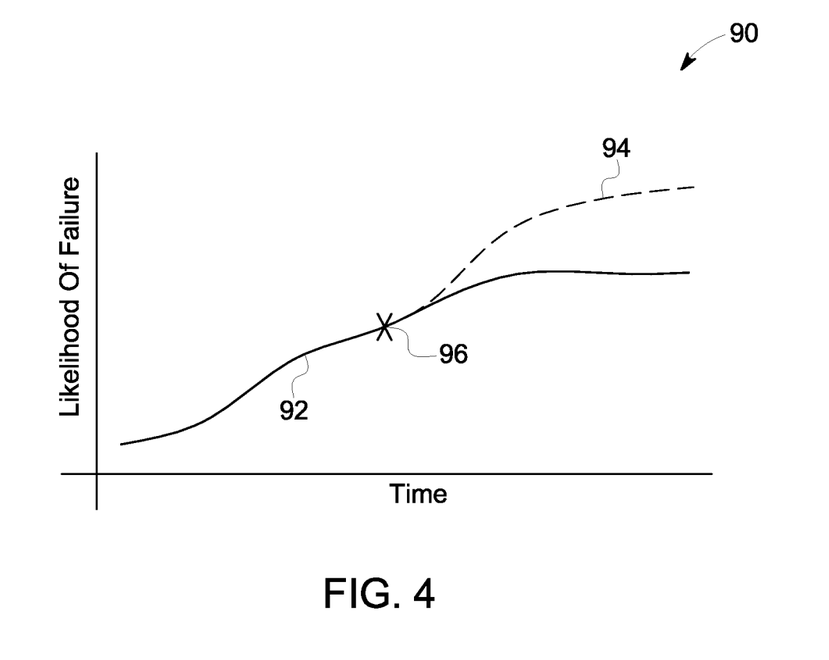
FIG. 4 is an exemplary graph that may be provided in accordance with various embodiments.

The non-uniformity information may be compiled and/or presented in any suitable manner. For example, as shown in FIG. 4, a graph 90 may be generated, which may be displayed to a user. The x-axis corresponds to time and the y-axis corresponds to a probe property, such as a likelihood of failure, probe imaging performance on an absolute or relative scale, etc. The graph 90 includes a curve 92 that corresponds to a change in the likelihood of failure (in the past) and predicted likelihood of failure (in the future) using the determined non-uniformity information and the method 60. The graph 90 may also include a curve portion 94 that represents and shows a change in the predicted probe property (e.g., useful life). In this case, the curve portion 94 illustrates that the likelihood of probe failure is on an increased track and also identifies a point 96 on the curve 92 corresponding to an identified or recorded event. In this case, the event may be a dropped probe, after which the likelihood of failure increased more rapidly, which may have resulted from damage to some transducer elements that may be determined based on the non-uniformity information.

Figure 5:
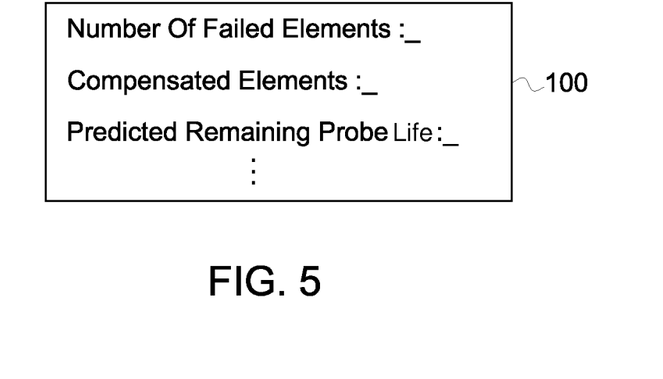
FIG. 5 is a diagram of an exemplary report that may be provided in accordance with various embodiments.

As another example, the non-uniformity information may be presented in a report 100 as shown in FIG. 5. The report 100 may be displayed or in hard copy form. The report 100 may include any information derived or determined from the measured non-uniformity information. For example, the report may identify the number of failed transducer elements, the number of transducer elements being compensated, the predicted remaining probe life, etc. In general, any desired or required information may be provided.

Thus, various embodiments may provide an ultrasound console that monitors the response of the individual transducer elements (or groups of transducer elements) during normal scanning, without the use of special test circuitry or test phantoms. The probe health optionally may be reported to the ultrasound operator, for example in the form of an indicator on a display, or as a warning to the operator if the probe performance drops below a predetermined acceptance threshold, as a performance trend vs. time as described herein, or other suitable formats. Alternately, the probe health information based on the measured transducer non-uniformity may be used to generate information that can be accessed by a service technician. This information may be accessed, for example, during scheduled maintenance sessions, either locally or over a network. Also, information about an individual probe's performance and/or performance trend may also be stored within a memory device that is located either in the system, and/or as a part of the probe assembly. The latter method allows the information to be accessed and used by other systems that may not have the monitoring capabilities of the various embodiments.

It should be noted that the various embodiments may also be used in connection with special test objects (e.g., phantoms) or test circuitry. Also, it should be noted that the receiver channels and the transmitter channels of the probe in various embodiments are initially calibrated. For example, the gains of all receiver channels are calibrated to be within a determined tolerance or variance, such as within a fraction of a dB. For example, the receiver gain may be calibrated during manufacture of the ultrasound system. Alternately, gain characteristics may be stored on the console (e.g., generated during manufacturing), and taken into account during both the array measurement and in the correction of the beamforming. It should be noted that a similar correction may be performed on the transmit side.

Figure 6:
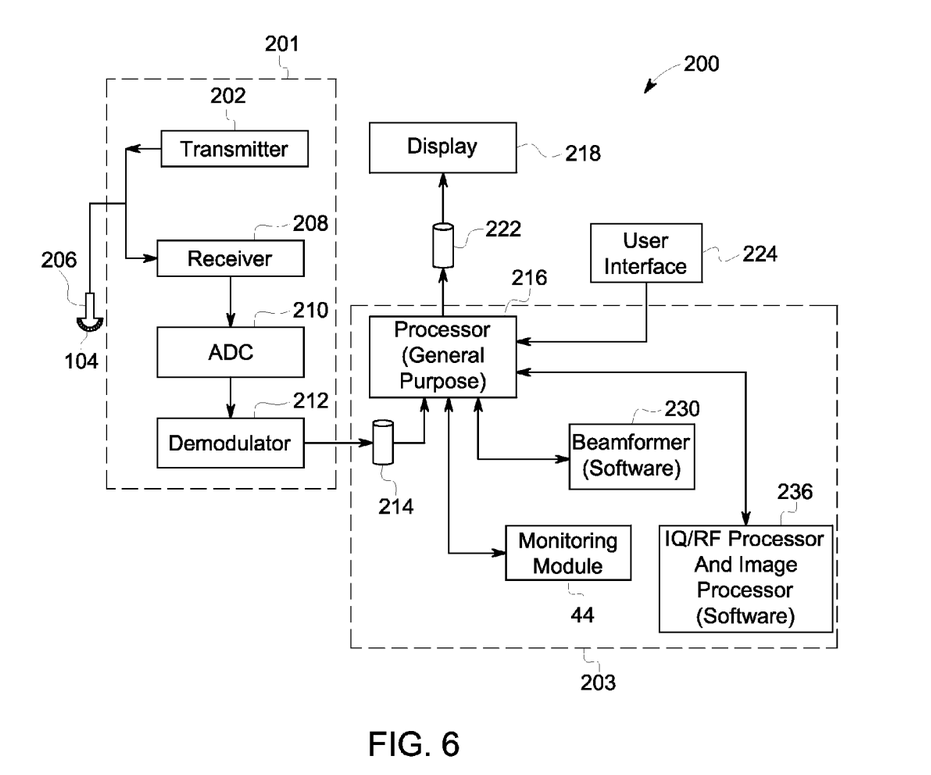
FIG. 6 is a block diagram of an ultrasound system in connection with which various embodiments may be implemented.

The various embodiments may be implemented in an ultrasound system 200 as illustrated in FIG. 6. It should be noted that the various embodiments may be implemented in different portions or components of the ultrasound system 200.

In particular, FIG. 6 is a block diagram showing an ultrasound system 200 that operates to perform transducer array monitoring in accordance with one or more embodiments described herein and also includes software beamforming. The monitoring operation and the software beamforming may be implemented, for example, by a processor executing instructions on a tangible, non-transitory computer readable medium. The ultrasound system 200 is configured to acquire ultrasound data using a probe 206, wherein transmission and reception of ultrasound signals are provided by a front end 201, which as illustrated does not include a hardware implemented receive beamformer. However, it should be noted that a hardware implemented receive beamformer optionally may be provided to perform some beamforming, for example partial beamforming. The front end 201 is connected to a back end 203 via a plurality of data channels that communicate ultrasound element data from the front end 201 to the back end 203.

The ultrasound system 200 is capable of electrical or mechanical steering of a sound beam (such as in 3D space) and is configurable to acquire information corresponding to a plurality of 2D representations or images (or optionally 3D and 4D images) of a region of interest (ROI) in a subject or patient, which may be defined or adjusted as described in more detail herein. The ultrasound system 200 is configurable to acquire 2D images, for example, in one or more planes of orientation.

The ultrasound system 200 includes a transmitter 202 that, under the guidance of a beamformer (transmit beamformer), drives an array of elements 204 (e.g., piezoelectric elements) within a probe 206 to emit pulsed ultrasonic signals into a body. A variety of geometries may be used. The ultrasonic signals are back-scattered from structures in the body, like blood cells or muscular tissue, to produce echoes that return to the elements 204. The echoes are received by a receiver 208 and then communicated to an ADC 210 and demodulator 212, which may be different components or implemented in a single component, for example, in an ASIC. The complex demodulator 212 performs digital demodulation, and optionally filtering and decimation as described in more detail herein. The demodulated (or down-sampled) ultrasound data may be stored in a memory 214, such as temporarily for access by the monitoring module 44 to perform one or more embodiments described herein. In another embodiment, the monitoring module 44 may be an integrated part of the beamformer 230 (also referred to as a beamformer module).

The complex demodulator 212, demodulates the RF signal to form IQ data pairs representative of the echo signals, which in various embodiments have a reduced data transfer rate that the transfer rate of the ADC 210. Alternately, the complex demodulator 212 may be removed or replaced by some other signal processing algorithm. The RF or IQ element data may then be routed directly to the memory 214 for storage. In some embodiments, a hardware receive beamformer optionally may be provided in the front end 201. In an alternative embodiment, the probe 206 optionally includes a 1D or 2D array with sub-aperture receive beamforming inside the probe.

The output signals from the beamformer 230 may be processed by a mid-processor 236 into different data types, e.g. B-mode, color Doppler (velocity/power/variance), tissue Doppler (velocity), and Doppler energy, for multiple scan planes or different scanning patterns. In one embodiment (as illustrated), the mid-processor 236 is embodied in software as an I,Q/RF processor and image processor. The processor 236 (also referred to as the ultrasound processor module) may generate tissue Doppler data for multi-scan planes. The processor 236 also may gather the information (e.g. I,Q data pairs, B-mode, color Doppler, tissue Doppler, and Doppler energy information) related to multiple data slices and stores the data information, which may include time stamp and orientation/rotation information, in the memory 214.

The ultrasound system 200 also includes a processor 216 to further process the output of the processor 236 and prepare frames of ultrasound information for display on display 218, with the image quality or resolution improved in some embodiments as described in more detail herein. The processor 216 is adapted to perform one or more processing operations according to a plurality of selectable ultrasound modalities on the acquired ultrasound data. The processor 216 also performs beamforming operations using a beamformer 230, which in one embodiment (as illustrated) is software. The processor 216 is connected to a user interface 224 (which may include a mouse, keyboard, touch panel, etc.) that may control operation of the processor 216 as explained below in more detail. A display 218 includes one or more monitors that present patient information, including diagnostic ultrasound images to the user for diagnosis and analysis, as well as monitoring information as described herein. One, two or all of the memory 214, a memory 223 (shown in FIG. 7) and the memory 222 may store data corresponding to two-dimensional (2D) or three-dimensional (3D) data sets of the ultrasound data, where such 2D and 3D data sets are accessed to present 2D (and/or 3D or 4D images), which may be in different states of processing. The images may be modified and the display settings of the display 218 also manually adjusted using the user interface 224.

The beamformer 230 shown connected to the processor 216 may be software running on the processor 216 or hardware provided as part of the processor 216. The beamformer 230, performs receive beamforming as described in more detail herein and outputs a signal of I,Q data pairs. The beamformer 230 may phase shift, delay, apodize and sum each element signal with other element signals. The summed signals represent echoes from the ultrasound beams or lines.

It should be noted that although the various embodiments may be described in connection with an ultrasound system, the methods and systems are not limited to ultrasound imaging or a particular configuration thereof. The various embodiments may be implemented in connection with different types of imaging systems, including, for example, multi-modality imaging systems having an ultrasound imaging system and one of an x-ray imaging system, magnetic resonance imaging (MRI) system, computed-tomography (CT) imaging system, positron emission tomography (PET) imaging system, among others. Further, the various embodiments may be implemented in non-medical imaging systems, for example, non-destructive testing systems such as ultrasound weld testing systems or airport baggage scanning systems.

Figure 7:
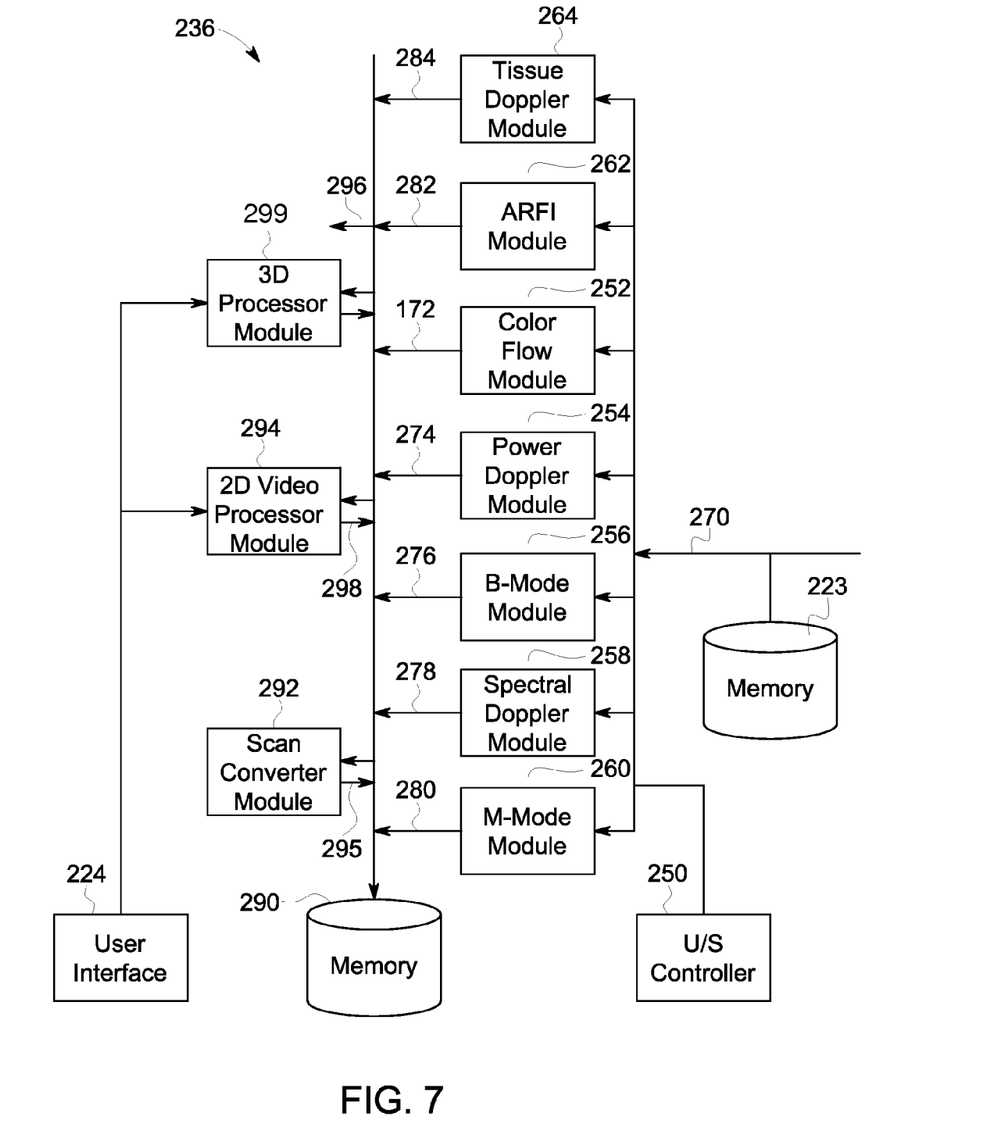
FIG. 7 is a block diagram of an ultrasound processor module of the ultrasound system of FIG. 6 formed in accordance with various embodiments.

FIG. 7 illustrates an exemplary block diagram of an ultrasound processor module 236, which may be embodied as the processor 216 of FIG. 6 or a portion thereof. The ultrasound processor module 236 is illustrated conceptually as a collection of sub-modules, but may be implemented utilizing any combination of dedicated hardware boards, DSPs, processors, etc. Alternatively, the sub-modules of FIG. 7 may be implemented utilizing an off-the-shelf PC with a single processor or multiple processors, with the functional operations distributed between the processors, for example also including a Graphics Processor Unit (GPU). As a further option, the sub-modules of FIG. 7 may be implemented utilizing a hybrid configuration in which certain modular functions are performed utilizing dedicated hardware, while the remaining modular functions are performed utilizing an off-the shelf PC and the like. The sub-modules also may be implemented as software modules within a processing unit.

Figure 9:
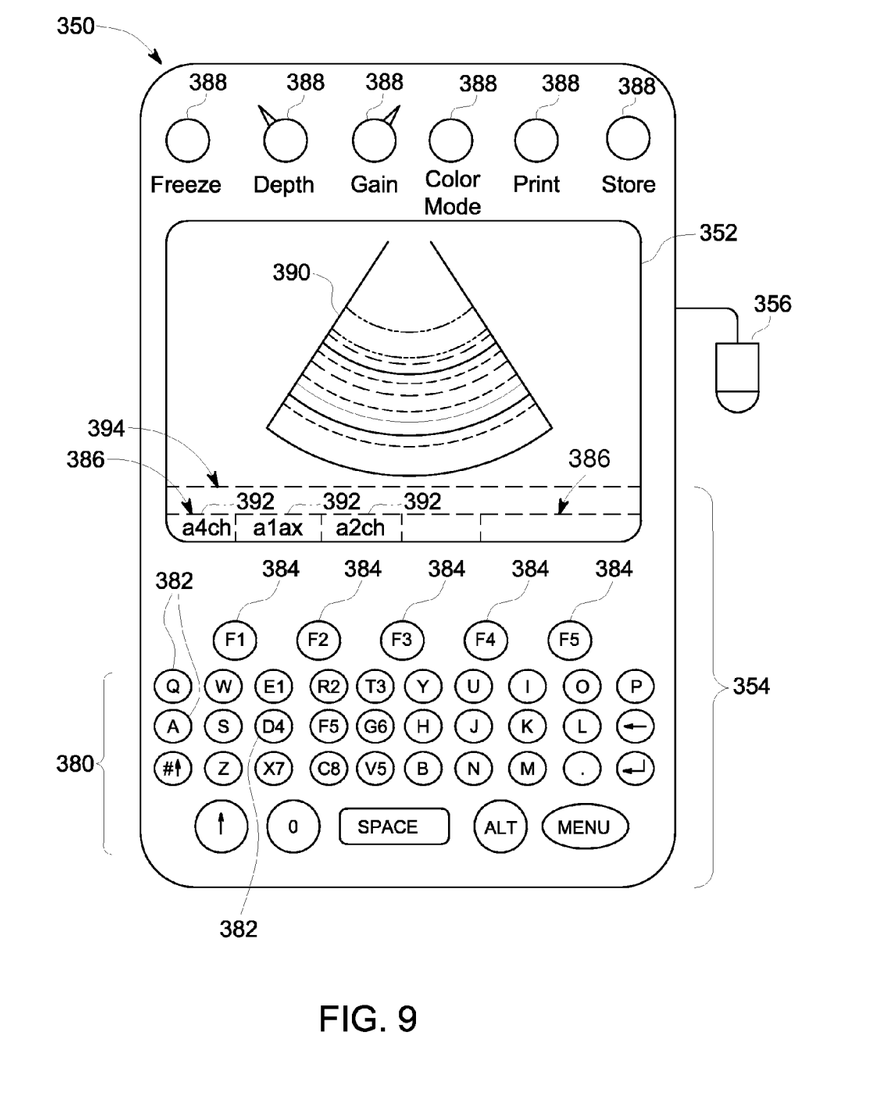
FIG. 9 is a diagram illustrating a hand carried or pocket-sized ultrasound imaging system in which various embodiments may be implemented.

The operations of the sub-modules illustrated in FIG. 7 may be controlled by a local ultrasound controller 250 or by the processor module 236. The sub-modules 252-264 perform mid-processor operations. The ultrasound processor module 236 may receive ultrasound data 270 in one of several forms. In the embodiment of FIG. 9, the received ultrasound data 270 constitutes I,Q data pairs representing the real and imaginary components associated with each data sample. The I,Q data pairs are provided to one or more of a color-flow sub-module 252, a power Doppler sub-module 254, a B-mode sub-module 256, a spectral Doppler sub-module 258 and an M-mode sub-module 260. Optionally, other sub-modules may be included such as an Acoustic Radiation Force Impulse (ARFI) sub-module 262 and a Tissue Doppler (TDE) sub-module 264, among others.

Each of sub-modules 252-264 are configured to process the I,Q data pairs in a corresponding manner to generate color-flow data 272, power Doppler data 274, B-mode data 276, spectral Doppler data 278, M-mode data 280, ARFI data 282, and tissue Doppler data 284, all of which may be stored in a memory 290 (or memory 214 or memory 222 shown in FIG. 8) temporarily before subsequent processing. For example, the B-mode sub-module 256 may generate B-mode data 276 including a plurality of B-mode image planes, such as in a biplane or triplane image acquisition as described in more detail herein.

The data 272-284 may be stored in the memory 290, for example, as sets of vector data values, where each set defines an individual ultrasound image frame. The vector data values are generally organized based on the polar coordinate system. Alternately or additionally the data may be stored as beamformed I,Q data in the memory 223.

A scan converter sub-module 292 accesses and obtains from the memory 290 the vector data values associated with an image frame and converts the set of vector data values to Cartesian coordinates to generate an ultrasound image frame 295 formatted for display. The ultrasound image frames 295 generated by the scan converter sub-module 292 may be provided back to the memory 290 for subsequent processing or may be provided to the memory 214 or the memory 222.

Once the scan converter sub-module 292 generates the ultrasound image frames 295 associated with, for example, B-mode image data, and the like, the image frames may be restored in the memory 290 or communicated over a bus 296 to a database (not shown), the memory 214, the memory 222 and/or to other processors.

The scan converted data may be converted into an X,Y format for video display to produce ultrasound image frames. The scan converted ultrasound image frames are provided to a display controller (not shown) that may include a video processor that maps the video to a grey-scale mapping for video display. The grey-scale map may represent a transfer function of the raw image data to displayed grey levels. Once the video data is mapped to the grey-scale values, the display controller controls the display 218 (shown in FIG. 6), which may include one or more monitors or windows of the display, to display the image frame. The image displayed in the display 118 is produced from image frames of data in which each datum indicates the intensity or brightness of a respective pixel in the display.

Referring again to FIG. 7, a 2D video processor sub-module 294 combines one or more of the frames generated from the different types of ultrasound information. For example, the 2D video processor sub-module 294 may combine a different image frames by mapping one type of data to a grey map and mapping the other type of data to a color map for video display. In the final displayed image, color pixel data may be superimposed on the grey scale pixel data to form a single multi-mode image frame 298 (e.g., functional image) that is again re-stored in the memory 290 or communicated over the bus 296. Successive frames of images may be stored as a cine loop in the memory 290 or memory 222 (shown in FIG. 6). The cine loop represents a first in, first out circular image buffer to capture image data that is displayed to the user. The user may freeze the cine loop by entering a freeze command at the user interface 224. The user interface 224 may include, for example, a keyboard and mouse and all other input controls associated with inputting information into the ultrasound system 200 (shown in FIG. 8).

A 3D processor sub-module 299 is also controlled by the user interface 124 and accesses the memory 290 to obtain 3D ultrasound image data and to generate three dimensional images, such as through volume rendering or surface rendering algorithms as are known. The three dimensional images may be generated utilizing various imaging techniques, such as ray-casting, maximum intensity pixel projection and the like.

Figure 8:
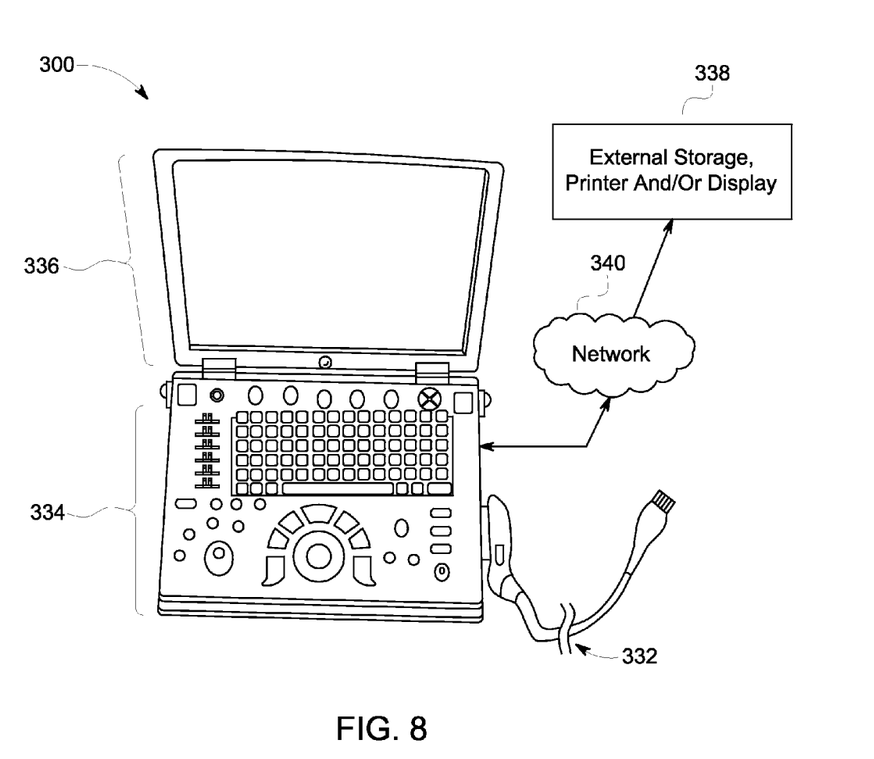
FIG. 8 is a diagram illustrating a miniaturized ultrasound system in which various embodiments may be implemented.
Figure 10:
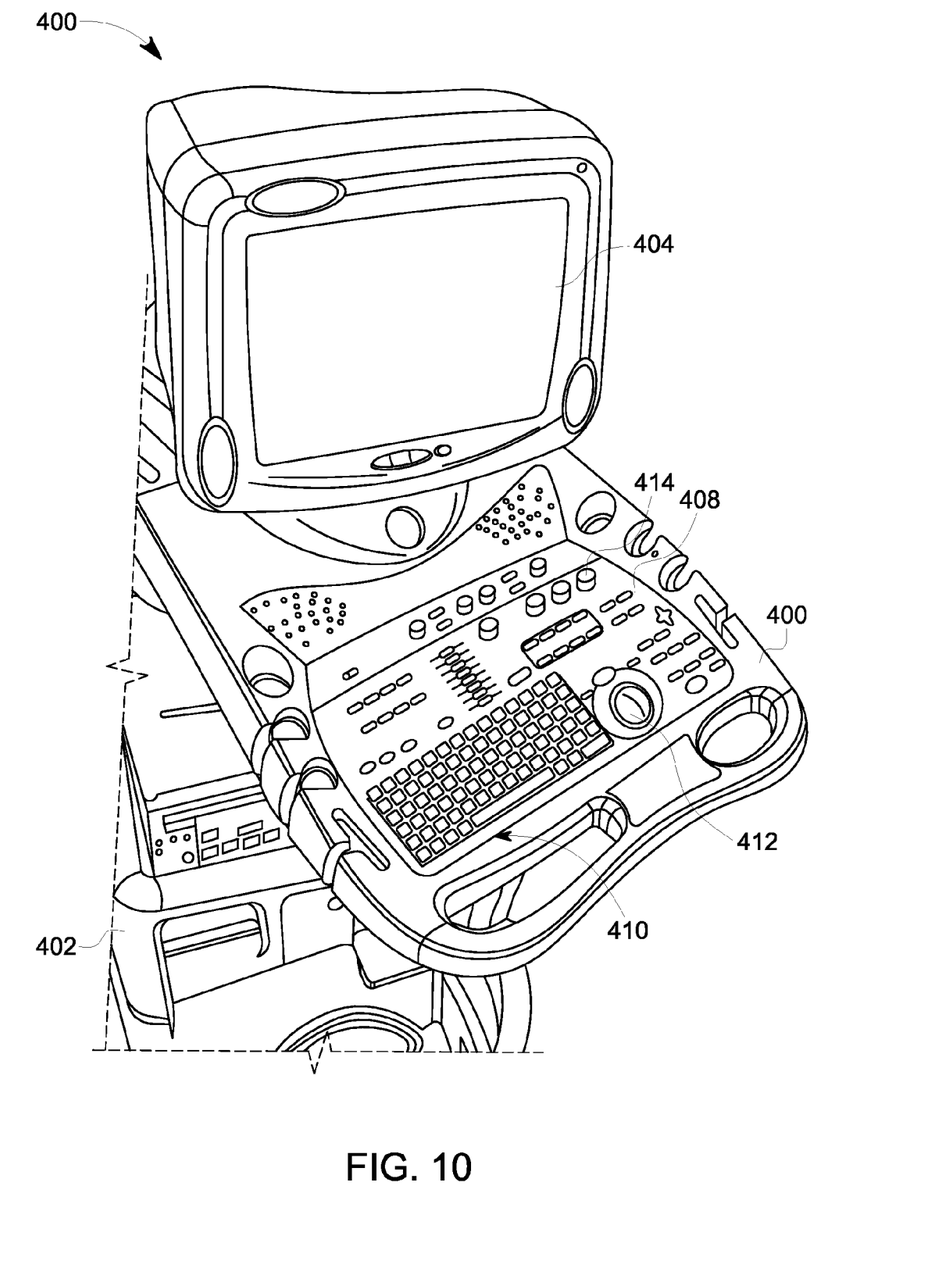
FIG. 10 is a diagram illustrating a console type ultrasound imaging system in which various embodiments may be implemented.

The ultrasound system 200 of FIG. 6 may be embodied in a small-sized system, such as laptop computer or pocket sized system as well as in a larger console-type system. FIGS. 8 and 9 illustrate small-sized systems, while FIG. 10 illustrates a larger system.

FIG. 8 illustrates a 3D-capable miniaturized ultrasound system 300 having a probe 332 that may be configured to acquire 3D ultrasonic data or multi-plane ultrasonic data. For example, the probe 332 may have a 2D array of elements 104 as discussed previously with respect to the probe 206 of FIG. 6. A user interface 334 (that may also include an integrated display 336) is provided to receive commands from an operator. As used herein, "miniaturized" means that the ultrasound system 330 is a handheld or hand-carried device or is configured to be carried in a person's hand, pocket, briefcase-sized case, or backpack. For example, the ultrasound system 330 may be a hand-carried device having a size of a typical laptop computer. The ultrasound system 330 is easily portable by the operator. The integrated display 336 (e.g., an internal display) is configured to display, for example, one or more medical images.

The ultrasonic data may be sent to an external device 338 via a wired or wireless network 340 (or direct connection, for example, via a serial or parallel cable or USB port). In some embodiments, the external device 338 may be a computer or a workstation having a display, or the DVR of the various embodiments. Alternatively, the external device 338 may be a separate external display or a printer capable of receiving image data from the hand carried ultrasound system 330 and of displaying or printing images that may have greater resolution than the integrated display 336.

FIG. 9 illustrates a hand carried or pocket-sized ultrasound imaging system 350 wherein the display 352 and user interface 354 form a single unit. By way of example, the pocket-sized ultrasound imaging system 350 may be a pocket-sized or hand-sized ultrasound system approximately 2 inches wide, approximately 4 inches in length, and approximately 0.5 inches in depth and weighs less than 3 ounces. The pocket-sized ultrasound imaging system 350 generally includes the display 352, user interface 354, which may or may not include a keyboard-type interface and an input/output (I/O) port for connection to a scanning device, for example, an ultrasound probe 356. The display 352 may be, for example, a 320×320 pixel color LCD display (on which a medical image 390 may be displayed). A typewriter-like keyboard 380 of buttons 382 may optionally be included in the user interface 354.

Multi-function controls 384 may each be assigned functions in accordance with the mode of system operation (e.g., displaying different views). Therefore, each of the multi-function controls 384 may be configured to provide a plurality of different actions. Label display areas 386 associated with the multi-function controls 384 may be included as necessary on the display 352. The system 350 may also have additional keys and/or controls 388 for special purpose functions, which may include, but are not limited to "freeze," "depth control," "gain control," "color-mode," "print," and "store."

One or more of the label display areas 386 may include labels 392 to indicate the view being displayed or allow a user to select a different view of the imaged object to display. The selection of different views also may be provided through the associated multi-function control 384. The display 352 may also have a textual display area 394 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 350 and the miniaturized ultrasound system 300 may provide the same scanning and processing functionality as the system 200 (shown in FIG. 6)

FIG. 10 illustrates an ultrasound imaging system 400 provided on a movable base 402. The portable ultrasound imaging system 400 may also be referred to as a cart-based system. A display 404 and user interface 406 are provided and it should be understood that the display 404 may be separate or separable from the user interface 406. The user interface 406 may optionally be a touchscreen, allowing the operator to select options by touching displayed graphics, icons, and the like.

The user interface 406 also includes control buttons 408 that may be used to control the portable ultrasound imaging system 400 as desired or needed, and/or as typically provided. The user interface 406 provides multiple interface options that the user may physically manipulate to interact with ultrasound data and other data that may be displayed, as well as to input information and set and change scanning parameters and viewing angles, etc. For example, a keyboard 410, trackball 412 and/or multi-function controls 414 may be provided.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive, solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for monitoring a transducer array of an ultrasound probe, the method comprising:
   acquiring ultrasound data using an ultrasound probe during an imaging mode of operation, the ultrasound data including echo information;
   comparing the echo information from a plurality of transducer elements of a transducer array of the ultrasound probe during the imaging mode of operation, the echo information being non-beamformed signal data; and
   determining non-uniformity information for the transducer array using the compared echo information during the imaging mode of operation.

2. The method of claim 1, further comprising using a threshold to determine valid ultrasound data for comparing.

3. The method of claim 1, further comprising averaging a function of the acquired ultrasound data over a determined time period.

4. The method of claim 3, wherein the function comprises a relative channel sensitivity.

5. The method of claim 1, further comprising determining probe health for the ultrasound probe using the determined non-uniformity information.

6. The method of claim 1, further comprising compensating for non-uniformities in one or more transducer elements of the plurality of transducer elements using the determined non-uniformity information.

7. The method of claim 1, further comprising quantifying an impact of non-uniformities using the determined non-uniformity information.

8. The method of claim 1, further comprising generating feedback information using the determined non-uniformity information.

9. The method of claim 8, wherein the feedback information is based in part on a detected probe event.

10. The method of claim 9, wherein the detected probe event is an excessive acceleration event.

11. The method of claim 1, further comprising creating trend information using the determined non-uniformity information.

12. The method of claim 1, further comprising storing the determined non-uniformity information and allowing access to the stored determined non-uniformity information by an ultrasound console not providing non-uniformity information.

13. The method of claim 1, further comprising updating probe information as a function of probe life using the determined non-uniformity information.

14. The method of claim 1, wherein comparing echo information comprises comparing signal amplitude information for at least a subset of the plurality of transducer elements.

15. The method of claim 1, wherein determining the non-uniformity information during the imaging mode of operation comprises performing the determination during ultrasound data acquisition.

16. The method of claim 1, wherein the comparing is performed on ultrasound data comprising data in a non-beamformed or non-image formed state.

17. The method of claim 1, further comprising determining one of a health state or performance index of the ultrasound probe using the determined non-uniformity information and storing the determined health state or performance index in a memory, wherein the determined health state or performance index is linked to the ultrasound probe.

18. An ultrasound system comprising:
an ultrasound probe having a transducer array for acquiring ultrasound data including echo information during an imaging mode of operation;
a memory for storing received echo information; and
a monitoring module for comparing the echo information from a plurality of transducer elements of the transducer array of the ultrasound probe during the imaging mode of operation, the stored echo information being non-beamformed signal data, the monitoring module also determining non-uniformity information for the transducer array using the compared echo information during the imaging mode of operation.

19. The ultrasound system of claim 18, wherein the monitoring module at least one of (i) uses apriori response data to predict an image quality deterioration, (ii) determines probe health for the ultrasound probe using the determined non-uniformity information, (iii) compensates for non-uniformities in one or more transducer elements of the plurality of transducer elements using the determined non-uniformity information, (iv) quantifies an impact of non-uniformities using the determined non-uniformity information; (v) generates feedback information using the determined non-uniformity information or (vi) creates trend information using the determined non-uniformity information.

20. The ultrasound system of claim 18, wherein the memory stores the determined non-uniformity information and allows access to the stored determined non-uniformity information by an ultrasound console not providing non-uniformity information.

21. The ultrasound system of claim 18, wherein the monitoring module compares signal amplitude information for at least a subset of the plurality of transducer elements.

22. A non-transitory computer readable storage medium for monitoring a transducer array of an ultrasound probe using a processor during an imaging mode of operation, the non-transitory computer readable storage medium including instructions to command the processor to:
compare echo information from a plurality of transducer elements of a transducer array of an ultrasound probe during the imaging mode of operation, the echo information being non-beamformed signal data; and
determine non-uniformity information for the transducer array using the compared echo information during the imaging mode of operation.

\* \* \* \* \*